United States Patent
Jones et al.

(10) Patent No.: US 11,873,367 B2
(45) Date of Patent: Jan. 16, 2024

(54) POLYMERS DEPOLYMERIZABLE BY METATHESIS OF A CLEAVABLE UNIT

(71) Applicant: National Technology & Engineering Solutions of Sandia, LLC, Albuquerque, NM (US)

(72) Inventors: Brad Howard Jones, Albuquerque, NM (US); Chad Lynn Staiger, Albuquerque, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 267 days.

(21) Appl. No.: 17/244,012

(22) Filed: Apr. 29, 2021

(65) Prior Publication Data

US 2021/0371575 A1 Dec. 2, 2021

Related U.S. Application Data

(60) Provisional application No. 63/031,366, filed on May 28, 2020.

(51) Int. Cl.
| | | |
|---|---|---|
| C08G 18/32 | (2006.01) | |
| C07C 6/04 | (2006.01) | |
| C08J 11/10 | (2006.01) | |
| C08G 18/78 | (2006.01) | |
| C08J 11/18 | (2006.01) | |
| C08G 18/72 | (2006.01) | |
| C08G 18/67 | (2006.01) | |
| C08J 11/28 | (2006.01) | |
| C08G 18/76 | (2006.01) | |

(52) U.S. Cl.
CPC ............ *C08G 18/3206* (2013.01); *C07C 6/04* (2013.01); *C08G 18/3212* (2013.01); *C08G 18/675* (2013.01); *C08G 18/725* (2013.01); *C08G 18/7621* (2013.01); *C08G 18/7664* (2013.01); *C08G 18/7831* (2013.01); *C08J 11/10* (2013.01); *C08J 11/18* (2013.01); *C08J 11/28* (2013.01); *C08G 2110/0008* (2021.01); *C08G 2110/0025* (2021.01); *C08G 2110/0083* (2021.01); *C08J 2375/14* (2013.01); *C08J 2375/16* (2013.01); *Y02W 30/62* (2015.05)

(58) Field of Classification Search
CPC ............ C08G 18/3206; C08G 18/3212; C08G 2110/0008; C08G 2110/0025; C08G 2110/0083; C08G 18/675; C08G 18/723; C08G 18/7664; C08G 18/7831; C08G 18/7621; C08G 18/725; C07C 6/04; C08J 11/10; C08J 2375/16; C08J 11/18; C08J 11/28; C08J 2375/14; Y02W 30/62
See application file for complete search history.

(56) References Cited

U.S. PATENT DOCUMENTS

| | | | | |
|---|---|---|---|---|
| 4,313,858 A | * | 2/1982 | Earing | .................. C08G 18/69 528/10 |
| 2018/0282524 A1 | * | 10/2018 | Chao | ...................... C08L 75/04 |

OTHER PUBLICATIONS

Abendroth, H. and Canji, E., "Anwendung der Metathese-Reaktion auf die Mikrostrukturbestimmung von Polybutadienen," Die MakrOmolekulare Chemie, 1975, vol. 176, pp. 775-779.

Coates, G. W. and Grubbs, R. S., "Quantitative Ring-Closing Metathesis of Polyolefins," Journal of American Chemical Society, 1996, vol. 118, pp. 229-230.

Watson, M. D. and Wagener, K. B., "Functionalized Polyethylene via Acyclic Diene Metathesis Polymerization: Effect of Precise Placement of Functional Groups," Macromolecules, 2000, vol. 33, pp. 8963-8970.

Dewaele, A. et al., "Depolymerzation of 1,4 Polybutadiene by Metathesis: High Yield of Large Macrocyclic Oligo (butadiene)s by Ligand Selectivity Control," Catalysis Science & Technology, 2016, vol. 6, pp. 7708-7717.

Hansen, N. et al., "Initial Steps of Aromatic Ring Formation in a Laminar Premixed Fuel-Rich Cyclopentene Flame," Journal of Physical Chemistry A, 2007, vol. 111, pp. 4081-4092.

Meloni, G. et al., "Enol Formation and Ring-Opening in OH-Initiated Oxidation of Cycloalkenes," Journal of Physical Chemistry A, 2008, vol. 112, pp. 13444-13451.

Neary, W. J. and Kennemur, J. G., "Polypentenamer Renaissance: Challenges and Opportunities," ACS Macro etters, 2019, vol. 8, pp. 46-56.

Song, K. et al., "Highly Active Ruthenium Metathesis Catalysts Enabling Ring-Opening Metathesis Polymerization of Cyclopentadiene at Low Temperatures," Nature Communications, 2019, vol. 10:3860, 9 pages.

(Continued)

*Primary Examiner* — Rabon A Sergent
(74) *Attorney, Agent, or Firm* — Kevin W. Bieg

(57) ABSTRACT

Novel polymers are depolymerizable by metathesis of a cleavable unit. As an example, a series of linear and crosslinked polyurethanes were prepared that can be selectively depolymerized under mild conditions. Two unique polyols were synthesized bearing unsaturated units in a configuration designed to favor ring-closing metathesis to five- and six-membered cycloalkenes. These polyols were co-polymerized with toluene diisocyanate to generate linear polyurethanes and trifunctional hexamethylene- and diphenylmethane-based isocyanates to generate crosslinked polyurethanes. The polyol design is such that the ring-closing metathesis reaction cleaves the backbone of the polymer chain. Upon exposure to dilute solutions of Grubbs' catalyst under ambient conditions, the polyurethanes were rapidly depolymerized to low molecular weight, soluble products bearing vinyl and cycloalkene functionalities. These functionalities enabled further re-polymerization by traditional strategies for polymerization of double bonds. This general approach can be expanded to develop a range of chemically recyclable condensation polymers that are readily depolymerized by orthogonal metathesis chemistry.

8 Claims, 8 Drawing Sheets

(56) References Cited

OTHER PUBLICATIONS

Hlil, A. R. et al., "Ring Opening Metathesis Polymerization (ROMP) of Five- to Eight-Membered Cyclic Olefins: Computational, Thermodynamic, and Experimental Approach," Journal of Polymer Science, Part A: Polymer Chemistry, 2017, vol. 55, pp. 3137-3145.
Jones, B. H. et al., "Selectively Depolymerizable Polyurethanes from Unsaturated Polyols Cleavable by Olefin Metathesis, Macromolecular Rapid Communications," 2021, vol. 42, 2000571, 8 pages.

* cited by examiner

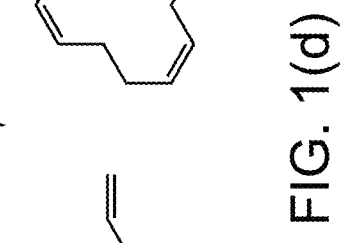
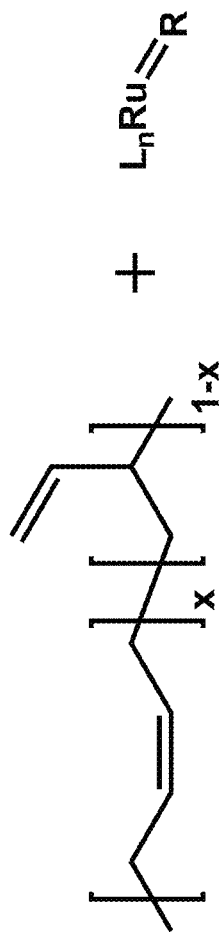
FIG. 1(a)
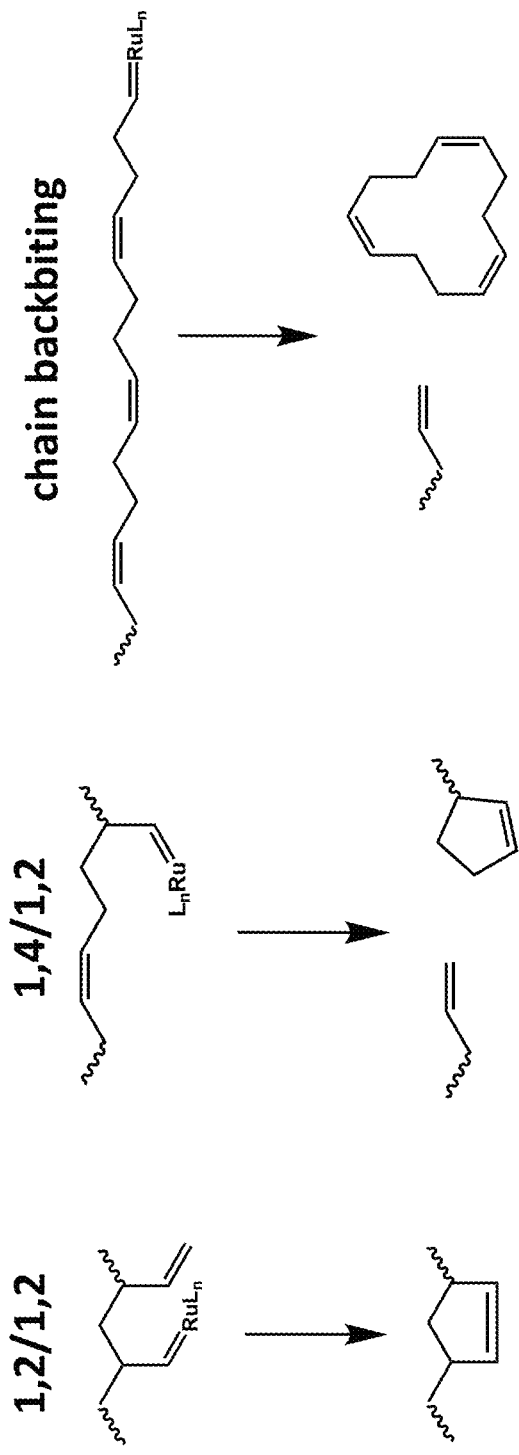
FIG. 1(d)
FIG. 1(c)
FIG. 1(b)

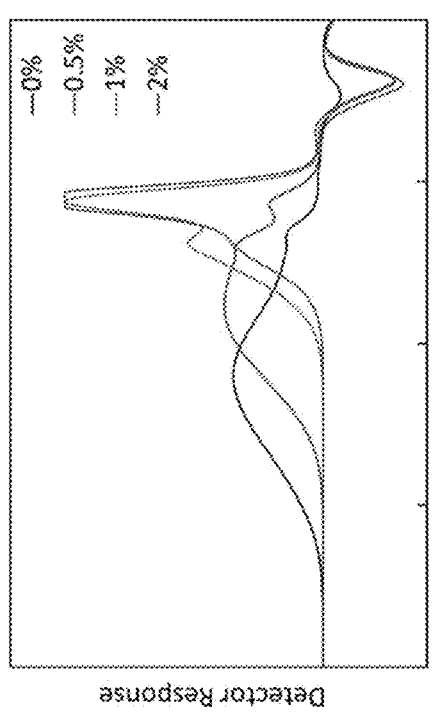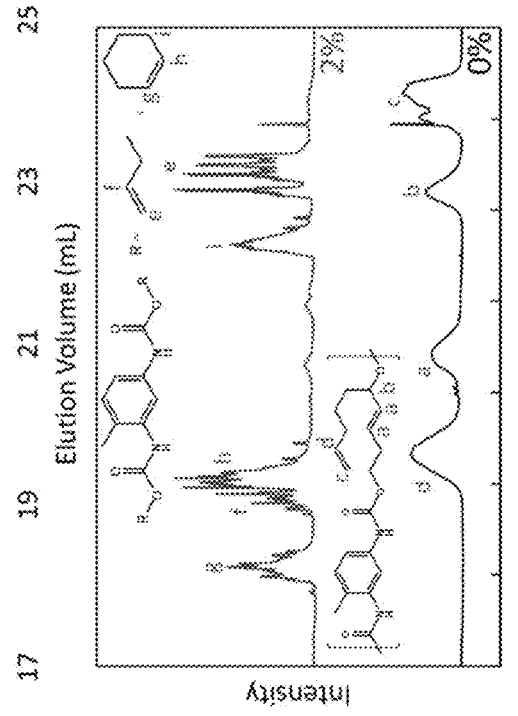
FIG. 5(a) FIG. 5(b) FIG. 5(c) FIG. 5(d)
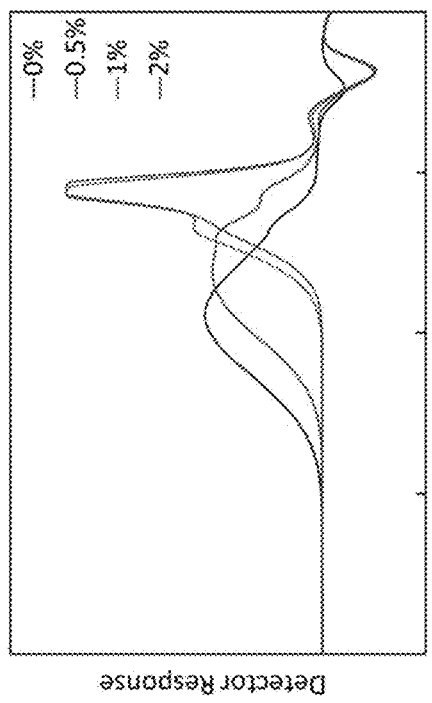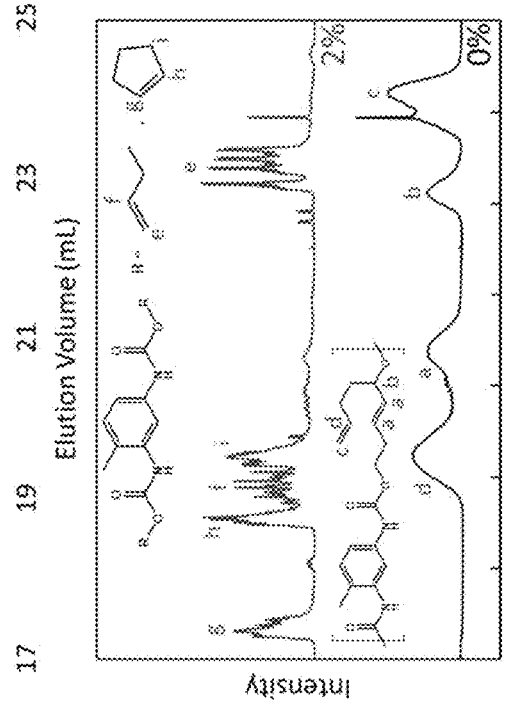

POLYMERS DEPOLYMERIZABLE BY METATHESIS OF A CLEAVABLE UNIT

CROSS-REFERENCE TO RELATED APPLICATION

This application claims the benefit of U.S. Provisional Application No. 63/031,366, filed May 28, 2020, which is incorporated herein by reference.

STATEMENT OF GOVERNMENT INTEREST

This invention was made with Government support under Contract No. DE-NA0003525 awarded by the United States Department of Energy/National Nuclear Security Administration. The Government has certain rights in the invention.

FIELD OF THE INVENTION

The present invention relates to recyclable plastics and, in particular, to novel polymers depolymerizable by metathesis of a cleavable unit.

BACKGROUND OF THE INVENTION

The management of polymer waste currently represents one of the most pressing environmental issues, as staggering quantities of non-degradable polymers accumulate in landfills and in the ocean. New approaches are needed whereby existing commodity polymers can be deconstructed into useful products in a highly selective and energy-efficient manner. Alternatively, new polymers are needed with property profiles matching existing commodity polymers, but that are deliberately designed to enable convenient and economical chemical recycling. Polyurethanes (PUs) provide a representative example in this regard. Found primarily in rigid and flexible foams, PUs account for nearly 10% of global consumption of polymers, a figure that has increased substantially over the last decade. See M. F. Sonnenschein, *Polyurethanes: Science, Technology, Markets, and Trends*; John Wiley & Sons, Inc., Hoboken, NJ (2015); and N. V. Gama et al., *Materials* 11, 1841 (2018). Unfortunately, the majority of PU waste is disposed of in landfills or by incineration, with various estimates indicating that only ca. 25-30% of PU waste is recycled. See M. Cregut et al., *Biotechnol. Adv.* 31, 1634 (2013); R. Gómez-Rojo et al., *Polymers* 11, 359 (2019); and R. V. Gadhave et al., *Open J. Polym. Chem.* 9, 39 (2019). Indeed, a recent popular news article illustrated the crux of the problem in highlighting the mounting volume of landfill waste from PU mattresses, driven by growth of online retailing and the ease with which mattresses can now be shipped. See S. Kale, "The Mattress Landfill Crisis: How the Race to Bring us Better Beds Led to a Recycling Nightmare," *The Guardian*, Feb. 12, 2020.

PUs are degradable by various routes—typically involving cleavage of the carbamate linkage—and can thus be chemically recycled. See N. V. Gama et al., *Materials* 11, 1841 (2018); K. M. Zia et al., *React. Funct. Polym.* 67, 675 (2007); and W. Yang et al., *Procedia Environ. Sci.* 16, 167 (2012). For example, hydrolysis of PUs can be employed in certain cases to recover the original alcohol monomer (polyol), along with the amine analogue of the original isocyanate monomer. See L. R. Mahoney et al., *Environ. Sci. Technol.* 8, 135 (1974); T. M. Chapman, *J. Polym. Sci. Polym. Chem.* 27, 1993 (1989); Z. Dai et al., *Polym. Degrad. Stabil.* 76, 179 (2002); S. Motokucho et al., *J. Polym. Sci. Polym. Chem.* 55, 2004 (2017); and S. Motokucho et al., *J. Appl. Polym. Sci.* 135, 45897 (2018). Similarly, various amines, alcohols, and acids have been used to displace the carbamate linkage and thereby depolymerize PUs. See K. Kanaya and S. Takahashi, *J. Appl. Polym. Sci.* 51, 675 (1994); J.-J. Ge and K. Sakai, *J. Wood Sci.* 44, 103 (1998); S. Chuayjuljit et al., *J. Met. Mater. Miner.* 12, 19 (2002); H. Watando et al., *Polym. Degrad. Stabil.* 91, 3354 (2006); X. Wang et al., *Fib. Polym.* 12, 857 (2011); M. Wang et al., *Prog. Rubber Plast. Recyc. Technol.* 30, 221 (2014); S. Bhandari and P. Gupta, In Recycling of Polyurethane Foams; S. Thomas et al., Eds.; William Andrew Publishing: Oxford, pp 77-87 (2018); C.-H. Wu et al., *Polym. Degrad. Stabil.* 80, 103 (2003); D. Simón et al., *Polym. Degrad. Stabil.* 116, 23 (2015); J. Paciorek-Sadowska et al., *J. Elastom. Plast.* 48, 340 (2016); R. Esquer and J. J. Garcia, *J. Organomet. Chem.* 902, 120972 (2019); D. Simón et al., *Waste Manage.* 76, 147 (2018); R. V. Gadhave et al., *Open J. Polym. Chem.* 9, 39 (2019); K. Troev et al., *J. Appl. Polym. Sci.* 78, 2565 (2000); K. Troev et al., *Polymer* 41, 7017 (2000); K. Troev et al., *Polym. Degrad. Stabil.* 67, 397 (2000); G. Grancharov et al., *J. Appl. Polym. Sci.* 105, 302 (2007); C. Molero et al., *J. Macromol. Sci. A* 47, 983 (2010); V. Mitova et al., *J. Macromol. Sci. A* 50, 774 (2013); and N. Gama et al., *Chem. Eng. J.* 395, 125102 (2020). Generally speaking, however, these depolymerization strategies are energy intensive, requiring high temperature, high pressure, and/or long reaction times, and they are inefficient, requiring stoichiometric quantities of cleavage reagents to yield complex mixtures of monomers and oligomers (i.e., incomplete depolymerization) that must be further separated and purified. Alternatively, the dynamic nature of the carbamate linkage has been exploited to enable reprocessing of PUs via catalysts familiar in PU polymerizations, namely tertiary amines, Lewis acids, and organotin compounds. See D. K. Schneiderman et al., *ACS Macro Lett.* 5, 515 (2016); P. Yan et al., *Macromol. Chem. Phys.* 218, 1700265 (2017); P. Yan et al., *RSC Adv.* 7, 26858 (2017); P. Yan et al., *J. Appl. Polym. Sci.* 135, 45784 (2018); D. J. Fortman et al., *Macromolecules* 52, 6330 (2019); J. P. Brutman et al., *J. Phys. Chem. B* 123, 1432 (2019); and D. T. Sheppard et al., *ACS Cent. Sci.* 6, 921 (2020). In a similar vein, polyhydroxyurethanes can be reprocessed through catalyst-free exchange of hydroxyl and carbamate functionalities. See D. J. Fortman et al., *J. Am. Chem. Soc.* 137, 14019 (2015); X. Chen et al., *Polym. Chem.* 8, 6349 (2017); D. J. Fortman et al., *J. Appl. Polym. Sci.* 134, 44984 (2017); X. Chen et al., *ACS Appl. Mater. Interf.* 11, 2398 (2019); and X. Chen et al., *Polymer* 178, 121604 (2019). However, reprocessing of PUs and polyhydroxyurethanes also requires high temperature and/or extended reaction times.

Olefin metathesis is an attractive route to depolymerization of unsaturated rubbers, critically enabled by the nuanced chain microstructure (1,4- and 1,2-addition products) characteristic of polydienes. See N. Kiattanavith and K. Hummel, *Polym. Degrad. Stabil.* 41, 1 (1993); K. Hummel et al., *Angew. Makromol. Chem.* 207, 137 (1993); E. Thorn-Csanyi and K. Ruhland, *Macromol. Chem. Phys.* 200, 1662 (1999); M. D. Watson and K. B. Wagener, *Macromolecules* 33, 1494 (2000); S. S. Solanky et al., *Macromol. Chem. Phys.* 206, 1057 (2005); K. L. Sedransk et al., *Polym. Degrad. Stabil.* 96, 1074 (2011); Y.-X. Lu and Z. Guan, *J. Am. Chem. Soc.* 134, 14226 (2012); Y.-X. Lu et al., *J. Am. Chem. Soc.* 134, 8424 (2012); A. Fainleib et al., *Polimeros* 23, 441 (2013); S. Ouardad and F. Peruch, *Polym. Degrad. Stabil.* 99, 249 (2014); B. Jiang et al., *Macromol. React. Eng.* 9, 480 (2015); S. Leimgruber and G. Trimmel, *Monatsh. Chem.* 146, 1081 (2015); A. Dewaele et al., *Catal.*

Sci. Technol. 6, 7708 (2016); R. F. Smith et al., *Green Chem.* 18, 3448 (2016); A. Mouawia et al., *ACS Sustain. Chem. Eng.* 5, 696 (2017); S. Daniele et al., *Polymer* 130, 143 (2017); X. Michel et al., *Eur. Polym. J.* 96, 403 (2017); C. Ai et al., *Macromol. Res.* 25, 461 (2017); P. Liu and C. Ai, *Ind. Eng. Chem. Res.* 57, 3807 (2018); and J. A. Herman et al., *ACS Appl. Polym. Mater.* 1, 2177 (2019). Adjacent double bonds in side- and main-chain configurations are ring-closed by ruthenium (Ru) carbenes (Grubbs' catalysts) to cyclopentene and cyclohexene species with concomitant cleavage of the polymer chain. See M. D. Watson and K. B. Wagener, *Macromolecules* 33, 1494 (2000); A. Dewaele et al., *Catal. Sci. Technol.* 6, 7708 (2016); and J. A. Herman et al., *ACS Appl. Polym. Mater.* 1, 2177 (2019). The further realization that cyclopentene, functionalized cyclopentenes, and other five-membered alkene rings can be ring-opened through judicious selection of reaction conditions has spawned recent development of polypentenamer elastomers and related materials, including networks with continuous recyclability through sequential ring-opening and ring-closing metathesis. See W. J. Neary and J. G. Kennemur, *Macromolecules* 50, 4935 (2017); S. Brits et al., *Polym. Chem.* 9, 1719 (2018); W. J. Neary et al., *ACS Macro Lett.* 7, 1080 (2018); H. Liu et al., *ACS Macro Left.* 7, 933 (2018); G. A. Guillory and J. G. Kennemur, *Eur. Polym. J.* 120, 109251 (2019); W. J. Neary and J. G. Kennemur, *ACS Macro Lett.* 8, 46 (2019); W. J. Neary et al., *J. Am. Chem. Soc.* 141, 14220 (2019); and J. D. Feist and Y. Xia, *J. Am. Chem. Soc.* 142, 1186 (2020).

However, there remains a need for new polymer architectures that enable facile depolymerization of the polymers by catalytic olefin metathesis.

SUMMARY OF THE INVENTION

The present invention is directed to a depolymerizable polymer comprising at least one monomeric unit that is cleavable by catalytic olefin metathesis. The at least one monomeric unit can comprise two or more double bonds, where at least one double bond is placed in a main-chain configuration and at least one double bond is placed in a side-chain configuration. The depolymerizable polymer can comprise a condensation polymer formed by reacting a functional group of the cleavable monomer with a different monomer. The functional group can comprise a hydroxyl, amino, epoxide, isocyanate, aldehyde, anhydride, carboxyl group, or other non-vinyl species. Specific examples of cleavable monomers include 8-hydroxylinalool (HLL), (E)-nona-3,8-diene-1,5-diol (DEDO5) and (E)-deca-3,9-diene-1,5-diol (DEDO6). The condensation polymer can comprise a polyurethane, polyamide, polyester, or any other polymer formed from a chemistry that preserves the double bond configuration of the cleavable unit. Depolymerization is accomplished by exposure of the polymer to a Grubbs' catalyst, cleaving the polymer chain by ring-closing metathesis of the double bonds.

As an example of the invention, unsaturated moieties were integrated into polyurethanes that enable the preparation of a range of linear and crosslinked polyurethanes that can be selectively depolymerized by olefin metathesis under very mild (ambient) conditions. Based on the orthogonal nature of the polymerization and depolymerization chemistries, metathesis depolymerization of these polyurethanes did not yield the original monomer(s), but rather a new set of low molecular weight products defined by cycloalkene and vinyl functionalities. This orthogonality offers a significant advantage in that depolymerization can only be effected through the deliberate introduction of a metathesis catalyst, which otherwise plays no role in polyurethane polymerization and processing. Furthermore, the aforementioned functionalities can be re-polymerized by traditional strategies for polymerization of double bonds. This general approach can be implemented in most all condensation polymers. As such, olefin metathesis can play an important role in the design of next-generation polymers with tunable property profiles that can be selectively and efficiently depolymerized.

BRIEF DESCRIPTION OF THE DRAWINGS

The detailed description will refer to the following drawings, wherein like elements are referred to by like numbers.

FIG. 1(a) illustrates the metathesis of polydienes by a generalized ruthenium carbine catalyst $L_nRu=R$. FIG. 1(b) illustrates the ring-closing metathesis of a diad of 1,2 units. FIG. 1(c) illustrates the ring-closing metathesis and chain cleavage of a diad of 1,4 and 1,2 units. FIG. 1(d) illustrates the ring-closing metathesis and chain cleavage of an extended sequence of 1,4 units. Wavy lines indicate continued polymer chains.

FIG. 5(a) is a GPC chromatograph of poly(TDI-co-DEDO5) neat and with added HG2 (indicated as a mol % relative to the quantity of double bonds). FIG. 5(b) is a GPC chromatograph of poly(TDI-co-DEDO6) neat and with added HG2. FIG. 5(c) shows $^1$H NMR spectra of poly(TDI-co-DEDO5) neat and with 2% added HG2. FIG. 5(d) shows $^1$H NMR spectra of poly(TDI-co-DEDO6) neat and with 2% added HG2. Note that the narrow resonance at 5.01 ppm in all NMR spectra is due to the impurity BHT.

FIGS. 7(c) and 8(d) are photographs showing the disintegration of crosslinked poly(PMDI-co-DEDO5) and poly(HDIB-co-DEDO5), respectively. Left images: initial monolithic sample immersed in 1 mg/mL HG2 in $CHCl_3$. The total amount of HG2 in the solutions shown was 2 mol % relative to the quantity of double bonds in the PU monoliths. Right images: Sample and immersion solution poured over filter paper after 48 h immersion.

DETAILED DESCRIPTION OF THE INVENTION

Figure 2:
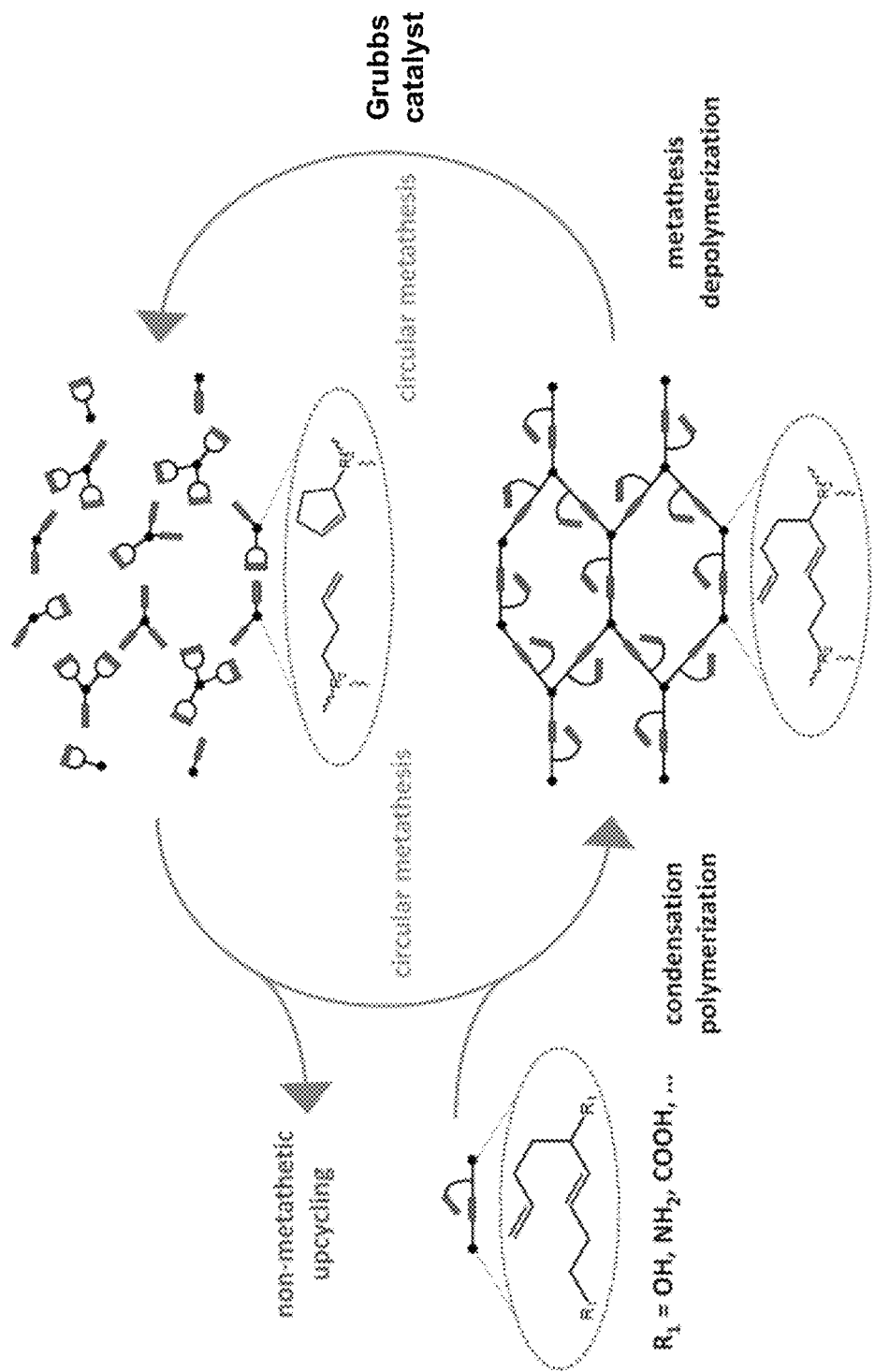
FIG. 2 is an illustration of a circular metathesis concept comprising the depolymerization of condensation polymers by chain cleavage through ring-closing olefin metathesis of precise double bond configurations and subsequent chemical upcycling.

The present invention is directed to a new class of polymer architectures, broadly applicable to a variety of classic and emerging polymer chemistries, with inherent capabilities for selective chemical deconstruction and reconstruction using catalytic olefin metathesis. As described above, olefin metathesis is a well-known chemical transformation involving redistribution of alkenes, typically by exchange of double bonds mediated by organometallic catalysts. Olefin metathesis is regarded as one of the most powerful catalytic reactions and, because of its relative simplicity, olefin metathesis often creates fewer undesirable by-products and is highly atom-economical compared to other organic reactions. Olefin metathesis has been applied for several decades in the depolymerization and functionalization of polydienes. The thermodynamics and kinetics of depolymerization of linear polydienes have been widely studied in solution and in bulk, while cross-metathesis of polydienes with functional alkenes has been demonstrated as an efficient route to telechelic polymers. Extensive depolymerization can be readily accomplished in these systems using catalyst loadings of far less than 1 mol. %.

As an example, the metathesis depolymerization of polybutadiene (PB) is enabled by the fortuitous arrangement of double bonds along the backbone and side chains of the polymer, such that ring-closing metathesis leads to the formation of relatively stable cyclic products and concomitant cleavage of the polymer chain. FIG. 1(a) illustrates the metathesis of polydienes by a generalized ruthenium (Ru) carbene (Grubbs' catalyst) $L_n Ru=R$. Three common products from PB metathesis by the generalized Ru carbene catalyst are shown in FIGS. 1(b)-(d). FIG. 1(b) illustrates the ring-closing metathesis of a diad of 1,2 units. FIG. 1(c) illustrates the ring-closing metathesis and chain cleavage of a diad of 1,4 and 1,2 units. This cleavage produces a pair of vinyl and cycloalkene products. FIG. 1(d) illustrates the ring-closing metathesis and chain cleavage of an extended sequence of 1,4 units. It is apparent that any PB material containing a non-negligible fraction of 1,4 units will experience a reduction in polymer chain length (i.e., depolymerization). See H. Abendroth and E. Canji, *Makromol. Chem.* 176, 775 (1975); G. W. Coates and R. H. Grubbs, *JACS* 118, 229 (1996); M. D. Watson and K. D. Wagener, *Macromolecules* 33, 1494 (2000); and A. Dewaele et al., *Catal. Sci. Technol.* 6, 7708 (2016).

Inspired by the metathesis of PB, the present invention is directed to methods of chemical upcycling that can be designed into a range of polymer chemistries. The monomers of the present invention retain a core, depolymerizable architecture, similar to that of PB, but with functional groups appended that enable polymerization by orthogonal means. As such, the resulting polymers can be catalytically deconstructed by metathesis, but also reconstructed by several pathways, metathetic and otherwise.

In principle, condensation polymers can be rendered universally depolymerizable with the high selectivity and catalytic efficiency typical of olefin metathesis. A comprehensive suite of novel, cleavable monomers and their corresponding depolymerizable polymers can be prepared. As will be described below, polyurethanes provide a model system for elucidating the effect of the chemical structure of the cleavable core unit, as well as the physical properties of the resultant polymer, on the kinetics and efficiency of subsequent depolymerization. For example, the size and associated ring strain of the cyclic product from ring-closing metathesis—which can be controlled through the cleavable monomer design—can critically affect depolymerization.

Depolymerization can occur in solution and in bulk, utilizing the ever-expanding arsenal of Ru carbene catalysts, for example. This approach can be extended to other polymer chemistries by variation of the orthogonal functionality, including epoxides, polyesters, and polyamides.

The products of depolymerization of these polymers are multi-functional olefins, and so traditional methods for olefin polymerization—for example, radical-based and thiol-ene polymerizations—can be used to reconstruct depolymerized mixtures into new polymers. Reconstruction pathways yielding polymers with similar physical and chemical properties in comparison to traditional polyolefins are preferred. In addition, the olefin nature of the depolymerized products can provide alternative opportunities for upcycling by olefin oxidation. These include catalytic transformation to useful synthetic intermediates, such as epoxides, alcohols, and aldehydes. See N. Hansen et al., *J. Phys. Chem. A* 111, 4081 (2007); and G. Meloni et al., *J. Phys. Chem. A* 112, 13444 (2008).

Preferably, condensation polymers can be designed with infinite chemical circularity through cyclic metathesis polymerization and depolymerization, as illustrated in FIG. 2. The low-strain cyclic olefin moieties present in the depolymerized products (e.g., the cyclopentene moiety shown in FIG. 2), while relatively stable, can in fact be polymerized by ring-opening metathesis with appropriate selection of catalyst and polymerization conditions. This realization has recently spawned development of a nascent class of polymers, polypentenamers, which can be reversibly polymerized and depolymerized at low and high temperatures, respectively, through sequential ring-opening and ring-closing of cyclopentene-based monomers. See W. J. Neary and J. G. Kennemur, *ACS Macro Lett.* 8, 46 (2019).

The present invention is directed to the reversible metathesis polymerization and depolymerization of condensation polymers. New catalysts have been developed that favor polymerization over depolymerization (and vice versa) with high conversions. See K. Song et al., *Nat. Commun.* 10, 3860 (2019). As before, the design of the initial cleavable monomer and its condensation chemistry critically impact the efficiency with which chemical circularity can be established. Therefore, systematic studies can probe the relationships between the chemical structures of the initial monomer and the polymer and the corresponding circular efficiency, as it relates to the properties of the reconstructed polymers. These studies can provide a deeper understanding of the fundamental science underpinning the circular metathesis of cyclic olefins. However, unlike the few existing examples of circular polyolefins (e.g., polypentenamers), the initial condensation chemistry applied in the present invention enables circularity to be incorporated into many different polymer classes with widely tunable final properties.

Figure 3:
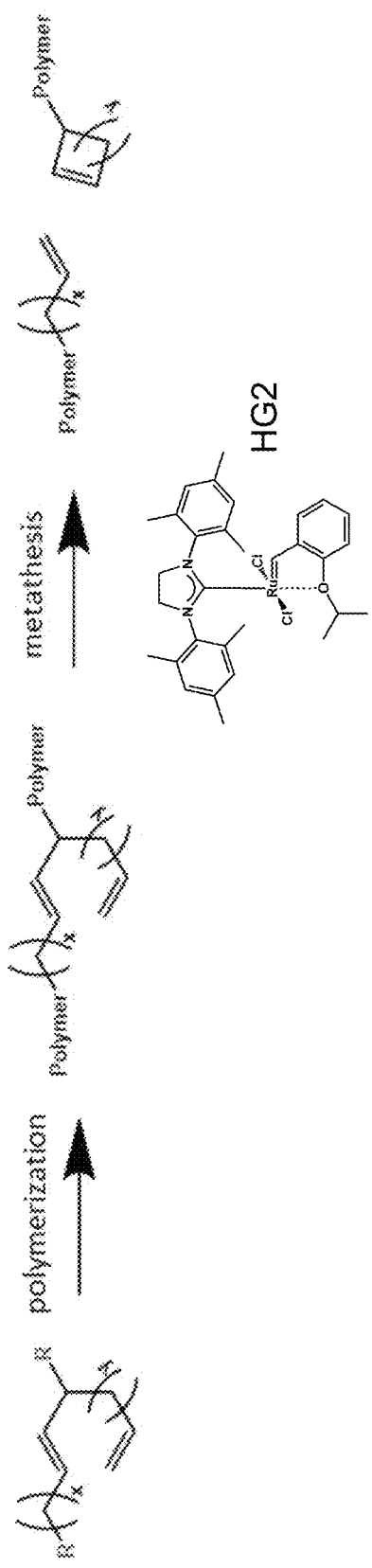
FIG. 3 illustrates a generalized monomer structure and approach to depolymerization by olefin metathesis.

The present invention is particularly directed to new polymers that are highly susceptible to metathesis depolymerization. These polymers are inspired by the molecular structure of PB, and are formed from monomers that possess cleavable, ring-closing moieties similar to those shown in FIGS. 1(b)-(d). A schematic illustration of a general co-polymer and its depolymerization according to the invention is shown in FIG. 3. The cleavable monomer is polymerizable by orthogonal chemistry with a different monomer into a co-polymer that can be subsequently depolymerized by metathesis. An exemplary cleavable monomer can comprise two or more double bonds, with one placed in a main-chain configuration and one placed in a side-chain configuration.

The monomer can also comprise functional groups (R in FIG. 3) that can be polymerized while preserving the double bonds and their architecture.

As an example of the invention, the catalytic degradation of polyurethanes (PUs) in which the PU is designed for efficient depolymerization under mild conditions is described below. In contrast to previous approaches, the example does not involve the cleavage or exchange of the carbamate linkage, but instead uses polyols that are cleavable by an orthogonal reaction. Specifically, an unsaturated polyol is used that readily undergoes ring-closing olefin metathesis.

Figures 4A, 4B, 4C:
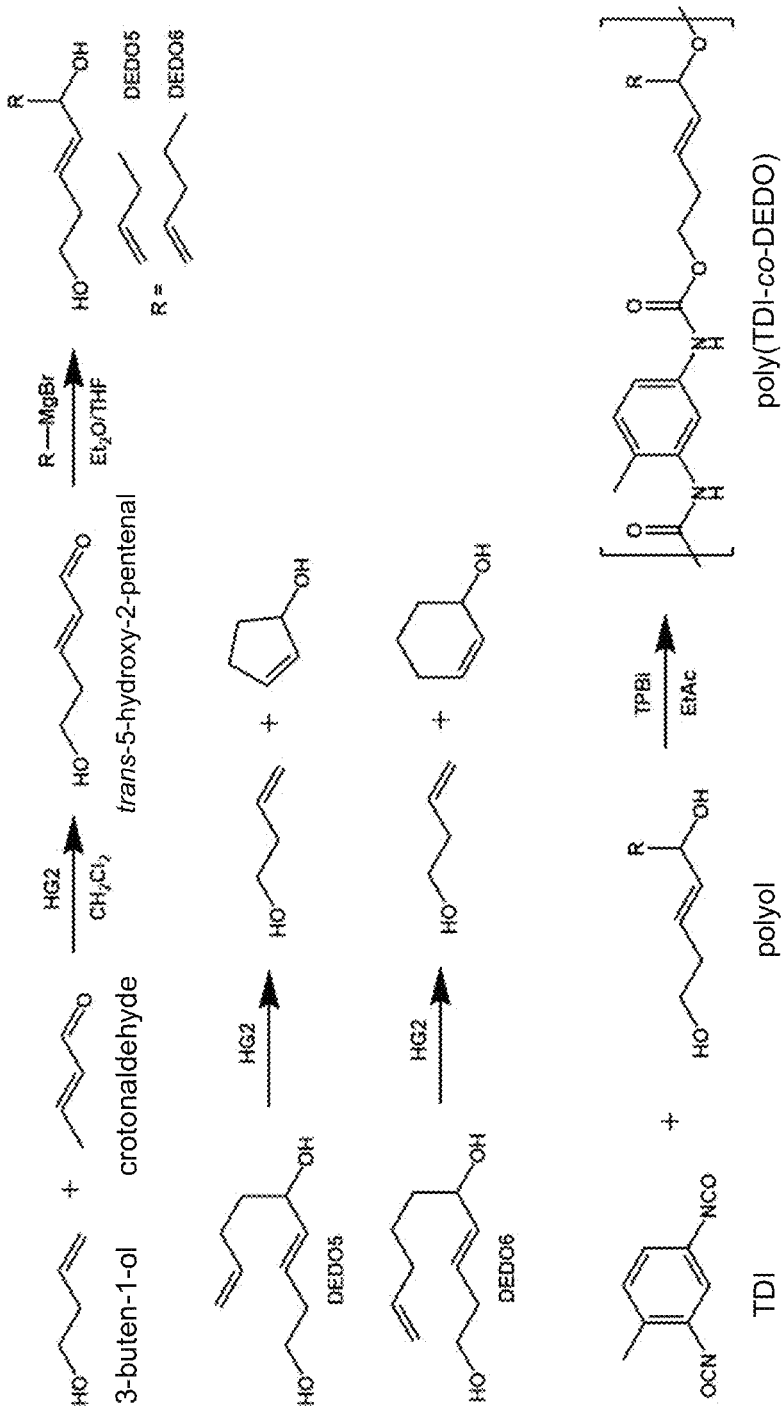
FIG. 4(a) illustrates the synthesis of unsaturated polyols DEDO5 and DEDO6.
FIG. 4(b) illustrates the ring-closing metathesis of the unsaturated polyols DEDO5 and DEDO6.
FIG. 4(c) illustrates the co-polymerization of DEDO5 or DEDO6 with TDI.

A two-step route to synthesize the unsaturated polyols (E)-nona-3,8-diene-1,5-diol (DEDO5) and (E)-deca-3,9-diene-1,5-diol (DEDO6), (DEDO indicating dienediol, and 5 and 6 indicating the targeted size of the ring-closed product, i.e., cyclopentene and cyclohexene, respectively) is shown in FIG. 4(a). The polyol monomers can be obtained from cross-metathesis of crotonaldehyde with 3-buten-1-ol, followed by coupling with the corresponding alkenyl Grignard reagent. In an exemplary synthesis, four equivalents of crotonaldehyde were combined with 3-buten-1-ol and then $2^{nd}$ generation Hoveyda-Grubbs catalyst (HG2, 0.8 mol %) was added in one portion. After vigorous evolution of propylene gas, the solution was stirred for an additional 20 h at room temperature. The solution was flash chromatographed on silica (100% $Et_2O$) to give trans-5-hydroxy-2-pentenal in 55% yield. In the final step to prepare DEDO5 or DEDO6, trans-5-hydroxy-2-pentenal was dissolved in $Et_2O$ and cooled to −10° C. Then 2.2 equivalents of either 3-butenylmagnesium bromide (for DEDO5) or 4-pentenylmagneisum bromide (for DEDO6) was added dropwise to the cooled solution over a period of 45 min. After stirring at −10° C. for 3 h, the solution was warmed to room temperature and stirred overnight. The solution was quenched with aqueous ammonium chloride and extracted with ethyl acetate (EtAc). The organic layer was dried ($MgSO_4$), filtered, and then concentrated using rotary evaporation. Flash chromatography on silica (100% $Et_2O$) gave DEDO5 and DEDO6 as a yellow oil in 42% and 39% yield, respectively.

These polyol monomers were chosen as examples due to the fact that five- and six-membered cycloalkenes possess exceptionally low ring strain; hence, ring closure of the double bond configuration was anticipated to be thermodynamically favorable. See A. R. Hlil et al., *J. Polym. Sci. A Polym. Chem.* 55, 3137 (2017). Indeed, solution $^1$H nuclear magnetic resonance (NMR) spectroscopy indicated quantitative cleavage of DEDO5 and DEDO6 to vinyl and cyclopentene or cyclohexene products, respectively, upon exposure to HG2, by ring-closing metathesis as shown in FIG. 4(b). There were also unmistakable signals attributable to ethylene byproduct and internal, non-cyclic alkenes, likely indicating further self-metathesis of the vinyl product (3-buten-1-op).

Next, linear poly(TDI-co-DEDO5) and poly(TDI-co-DEDO6) were prepared by co-polymerization of the unsaturated polyols with a common isocyanate, toluene diisocyanate (TDI), as shown in FIG. 4(c). In an exemplary procedure, ethyl acetate (EtAc) was first dried over 3 Å molecular sieves. TDI and DEDO5 or DEDO6 were dissolved in dry EtAc in amounts corresponding to equimolar isocyanate and alcohol reactive functional groups, r=[NCO]/[OH]=1. The concentration of monomer was 10% wt/vol. Triphenylbismuth (TPBi) was added as a polymerization catalyst at 2% (relative to wt monomer), and the reaction mixture was magnetically stirred at 50° C. overnight. The resulting polymers were recovered by removing the EtAc solvent under vacuum.

The resultant polymers, poly(TDI-co-DEDO5) and poly(TDI-co-DEDO6), were soluble in a variety of polar and non-polar solvents, including chloroform ($CHCl_3$), tetrahydrofuran (THF), and EtAc. Their molecular weight averages were on the order of several kg/mol, as shown in Table 1, with polydispersity indices of 1.5-2, consistent with typical step-growth linear polymerizations. Furthermore, the glass transition temperatures, $T_g$, of both polymers were near 60° C.

TABLE 1

Key characteristics of TDI-based depolymerizable PUs.

| | $M_n$ (kg/mol)[a] | $M_w$ (kg/mol)[b] | PDI[c] | $T_g$ (° C.)[d] |
|---|---|---|---|---|
| Poly(TDI-co-DEDO5) | 3.8 | 6.0 | 1.6 | 63 |
| Poly(TDI-co-DEDO6) | 5.9 | 12 | 2.0 | 61 |

[a]Number-averaged molecular weight
[b]Weight-averaged molecular weight
[c]Polydispersity index
[d]Glass transition temperature To depolymerize the linear polymers poly(TDI-co-DEDO5) and poly(TDI-co-DEDO6), the polymer was first dissolved in THF at 10% (w/v). Separately, HG2 was dissolved in THF at 1% (w/v). An appropriate portion of HG2 solution was added to the polymer solution to achieve a desired catalyst loading (0.5%, 1%, or 2%, expressed as a mol % relative to the quantity of double bonds). The solution was incubated under ambient conditions for 1 h, after which the metathesis reaction was terminated by addition of a large excess of ethyl vinyl ether (~100× by mol). The addition of ethyl vinyl ether was intended to ensure elimination of all active catalyst as a precaution for subsequent GPC analysis. The TDI-based PUs were rapidly depolymerized in solution upon exposure to HG2, as indicated by a combination of gel permeation chromatography (GPC) and $^1$H NMR spectroscopy. With increasing catalyst content, the GPC chromatographs of poly(TDI-co-DEDO5) and poly(TDI-co-DEDO6) indicate a progressive shift to lower molecular weight, as shown in FIGS. 5(a) and 5(b). At 2 mol % HG2 relative to the PU double bonds, depolymerization is effectively complete, with a narrow elution profile indicative of species of low molecular weight (<500 g/mol). The calculated molecular weight characteristics of the depolymerized samples are provided in Table 2.

TABLE 2

Molecular weight characteristics of depolymerized linear PUs.

| | HG2 (mol %)[a] | $M_n$ (kg/mol) | $M_w$ (kg/mol) | PDI |
|---|---|---|---|---|
| Poly(TDI-co-DEDO5) | 0 | 3.8 | 6.0 | 1.6 |
| | 0.5 | 1.6 | 2.9 | 1.8 |
| | 1 | 0.3 | 0.4 | 1.3 |
| | 2 | N/C[b] | N/C | N/C |
| Poly(TDI-co-DEDO6) | 0 | 5.9 | 12 | 2.0 |
| | 0.5 | 1.9 | 4.2 | 2.2 |
| | 1 | 0.4 | 0.5 | 1.3 |
| | 2 | N/C | N/C | N/C |

[a]Expressed relative to mol double bonds
[b]N/C indicates insufficient light scattered intensity to permit calculation Based on the orthogonal nature of the metathesis reaction, quantitative depolymerization of these PUs should yield a mixture of dicarbamates bearing various combinations of vinyl and cyclopentene or cyclohexene (for poly(TDI-co-DEDO5) and poly(TDI-co-DEDO6), respectively) terminal functionalities. Indeed, at 2 mol % added HG2, the $^1$H NMR spectra in FIGS. 5(c) and 5(d) clearly confirm this outcome, based on the assignment of unsaturated $^1$H resonances as indicated. These assignments are consistent with a previous report detailing the synthesis and NMR characterization of unsaturated monocarbamates bearing analogous structures to the dicarbamates of interest presently. See T. J. Donohoe et al., *J. Am. Chem. Soc.* 124, 12934 (2002). Quite conveniently, in contrast to the outcome of metathesis of the DEDO5 and DEDO6 monomers, the $^1$H NMR spectra of the corresponding depolymerized PUs show no evidence of additional self- or cross-metathesis of the depolymerization products. At 2 mol % HG2, the original resonances corresponding to the unsaturated portion of the PU repeat units were almost imperceptible by NMR spectroscopy. This observation confirms that near quantitative depolymerization of the PUs occurred in solution upon exposure to HG2 at the maximum concentration investigated. More precisely, by integration of resonances c and g in FIGS. 5(c) and 5(d), it was estimated that 95% of the poly(TDI-co-DEDO5) repeat units and 88% of the poly(TDI-co-DEDO6) repeat units were cleaved by ring-closing metathesis.

Corroborating this conclusion, gas chromatography/mass spectrometry (GC/MS) was performed on the linear, TDI-based PUs with and without 2 mol % added HG2. In a scenario where 100% of the repeat units are cleaved, the depolymerized PUs would consist of three distinct products bearing either two vinyl, two cycloalkene, or a pair of vinyl and cycloalkene terminal functionalities. The GC/MS analysis of both depolymerized PUs clearly indicated the presence of a species of mass 318 Da, matching the expected product bearing two vinyl functionalities. Furthermore, in the case of depolymerized poly(TDI-co-DEDO6), a species of mass 344 Da was detected, matching the expected product bearing vinyl and cyclohexene functionalities. It is unclear as to precisely why the expected product bearing two cycloalkene functionalities was not observed in either case. However, the depolymerized mixtures possessed a Fischer-type Ru carbene (i.e., the catalyst reacted with ethyl vinyl ether), which can still be metathesis-active under certain conditions. See J. Louie and R. H. Grubbs, *Organometallics* 21, 2153 (2002). Therefore, it is possible that the cycloalkene functionalities may have undergone further reaction during GC/MS analysis.

Figure 6:
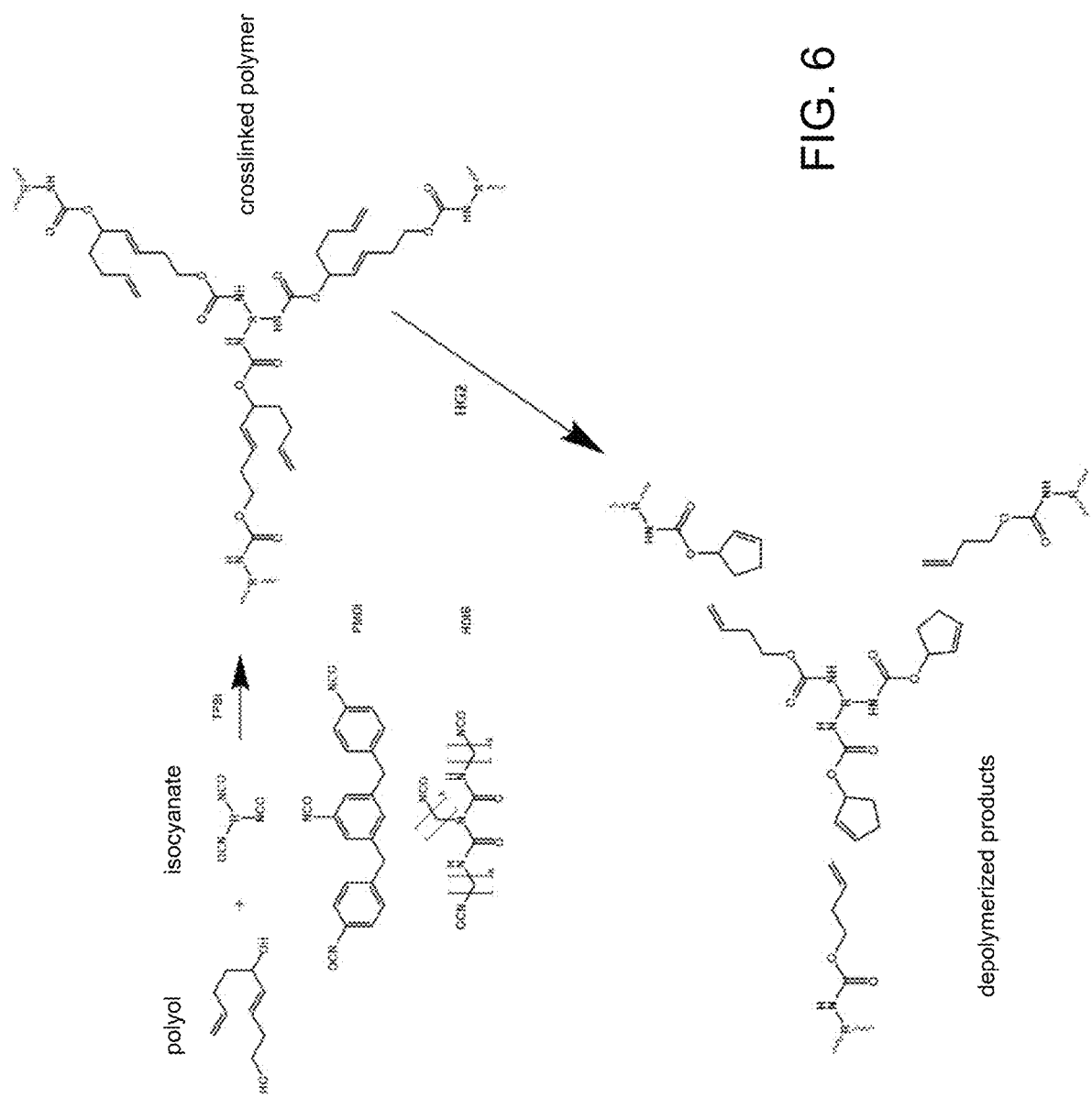
FIG. 6 illustrates the synthesis and metathesis depolymerization of crosslinked PUs. Wavy lines indicate continued polymer chains.

The above description demonstrates the depolymerization of linear PUs by olefin metathesis. Next, crosslinked PUs were prepared using the same unsaturated polyols. In order to prepare flexible and rigid PUs, the polyols were co-polymerized with the biuret of hexamethylenediisocyanate (HDIB, isocyanate functionality n=3) and polymeric diphenylmethanediisocyanate (PMDI, n=2.7), respectively, as shown in FIG. 6. Crosslinked polymers were prepared by hand-mixing a stoichiometrically balanced (r=1) amount of either PMDI or HDIB and DEDO5 or DEDO6, as well as 1 wt. % TPBi as a polymerization catalyst. For PMDI-based polymers, the polymerization was conducted at 100° C. for a minimum of 16 h. For HDIB-based polymers, the polymerization was conducted at 70° C. for a minimum of 16 h. The polyol and isocyanate co-monomers were fully miscible, enabling their convenient combination and polymerization by a solvent-free process. Both DEDO5 and DEDO6 were used to prepare crosslinked PUs in this manner, yielding qualitatively identical results. Here, DEDO5-based crosslinked PUs are provided as illustrative examples.

Figure 7A:
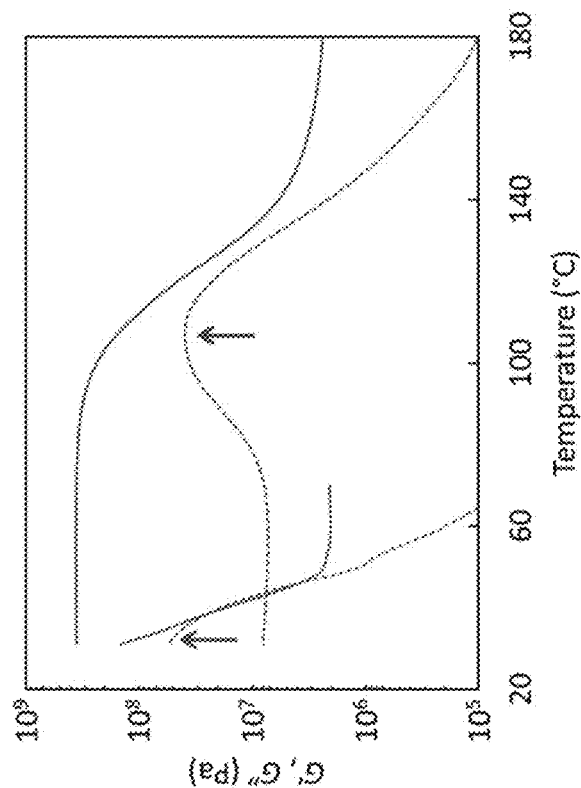
FIG. 7(a) is a graph of dynamic shear moduli (G'—solid, G"—dashed) measured during polymerization of DEDO5 with HDIB (polymerization temperature 70° C.) or PMDI (polymerization temperature 100° C.).
Figure 7B:
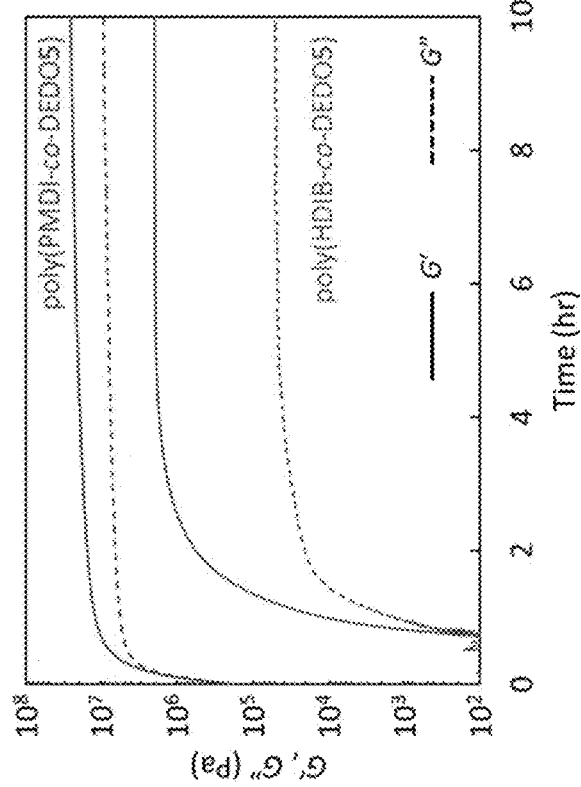
FIG. 7(b) is a graph of dynamic shear moduli measured after polymerization as a function of temperature (ramp rate: 3° C./min). $T_g$ is marked by the arrows.
Figure 7C:
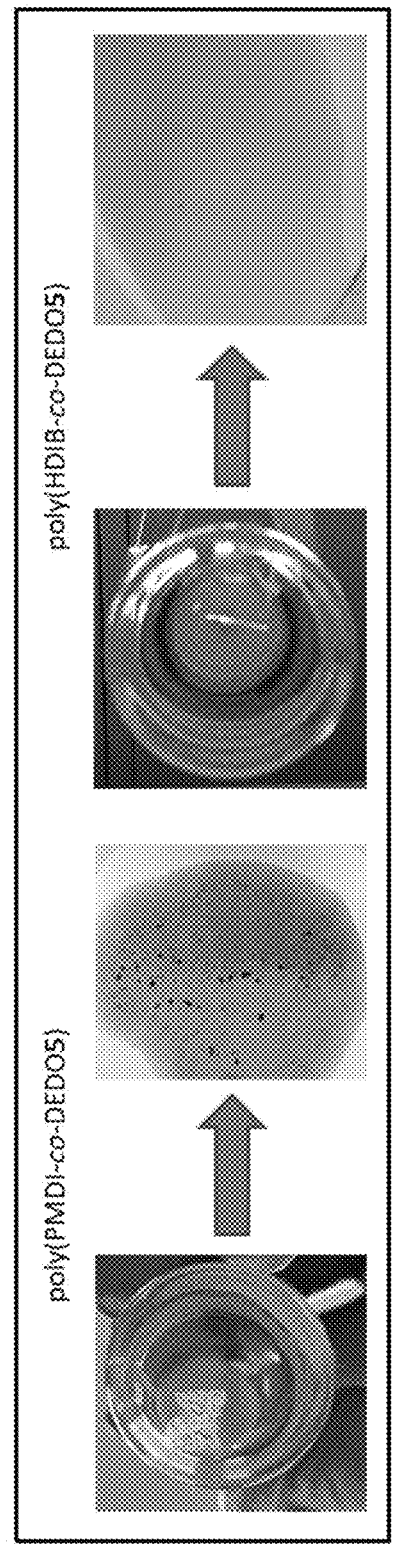

With 1 wt. % added polymerization catalyst, the crosslinking polymerization was complete within several hours as assessed by dynamic mechanical analysis (DMA), as shown in FIG. 7(a). The resultant monolithic HDIB-based PUs were transparent and flexible under ambient conditions, while the PMDI-based PUs were opaque and glassy, as shown in FIG. 7(c). The opacity of the latter was attributed to porosity due to partial reaction of the PMDI isocyanate functionality with residual water in the polymerization mixture and consequent liberation of $CO_2$ (i.e., foaming). PMDI is most frequently used in the production of rigid PU foams, in which water is deliberately added as a blowing agent. See W. J. Seo et al., *J. Appl. Polym. Sci.* 93, 2334 (2004); and M. Thirumal et al., *J. Appl. Polym. Sci.* 108, 1810 (2008). No attempt was made to further remove or control the water content of the polymerization mixture, as the primary interest was subsequent depolymerization. As shown in FIG. 7(b), the values of $T_g$ of the HDIB- and PMDI-based PUs were 33° C. and 107° C., respectively, reported as the temperature at which the dynamic loss modulus, G", achieves its maximum value. Both PUs exhibited rubbery storage moduli, $G'_r$, on the order of 2-3 MPa, indicating a relatively high density of crosslinks in the materials.

Unsurprisingly, the crosslinked PUs can be efficiently broken down upon immersion in a dilute solution of HG2, as shown in FIG. 6. For crosslinked polymers, a monolithic sample (50-100 mg) was placed in 5 mL total volume of a solution of 1 mg/mL HG2 in $CHCl_3$ or THF. The weight of the monolithic sample used was selected such that the total amount of HG2 in solution was 2 mol. % relative to the quantity of double bonds in the monolith. The sample was incubated under ambient conditions for 48 h, after which the metathesis reaction was terminated by addition of a large excess of ethyl vinyl ether (~100× by mol).

Again, the same behavior was observed with both DEDO5 and DEDO6-based PUs. Once exposed, the catalyst solution rapidly changed color from green to yellow and ultimately brown, consistent with activation and consumption of the catalyst. Control samples immersed in neat $CHCl_3$ swelled slightly due to uptake of solvent, but were otherwise unaffected. In contrast, HDIB-based PUs became fully soluble in the catalyst solution, indicating extensive cleavage of the polymer network to fragments of finite molecular weight. Indeed, $^1$H NMR spectra of the soluble products revealed the same unsaturated resonances as in FIGS. 5(c) and 5(d), demonstrating that depolymerization of the crosslinked PUs proceeds according to the same mechanism as the linear PUs, specifically, through ring-closing metathesis of the unsaturated component of the network. The PMDI-based PUs did not become fully soluble in catalyst solution in $CHCl_3$, rather the monoliths spontaneously fragmented into a coarse powder. The primary product of depolymerization in these particular cases—PMDI carbamates terminated with cycloalkene and vinyl functionalities—were simply insoluble in $CHCl_3$. Indeed, when the PMDI-based PUs were alternatively depolymerized in THF, soluble products were obtained. GPC analysis of the depolymerized mixtures obtained from both poly(PMDI-co-DEDO5) and poly(PMDI-co-DEDO6) revealed a broad distribution of low molecular weight products, consistent with extensive fragmentation of the PU networks.

These results clearly demonstrate a new, unique approach to degradation of PUs and a potentially viable solution to management of PU waste. However, the catalyst loadings used presently represent an added cost (2 mol. % HG2 corresponds to ca. 80 g catalyst per 1 kg PU), in addition to the required synthesis of non-traditional polyols. Therefore, further optimization is desirable from an economic standpoint. Along these lines, it has been previously shown that embedding latent metathesis catalysts in polybutadiene elastomers enables their solvent-free depolymerization to oils at extremely low catalyst loadings—two orders of magnitude lower (0.02 mol. %) than used at present (2 mol. %). See J. A. Herman et al., *ACS Appl. Polym. Mater.* 1, 2177 (2019). Moreover, metathesis catalysts can potentially be recovered and recycled in order to recover a fraction of their added cost. Several groups have demonstrated recyclability of metathesis catalysts, including HG2, by column chromatography. See J. S. Kingsbury et al., *J. Am. Chem. Soc.* 121, 791 (1999); A. Michrowska et al., *Chem. Commun.*, 841 (2006); and M. Matsugi et al., *J. Org. Chem.* 75, 7905 (2010). A pertinent review article has summarized various efforts towards catalyst reuse, such as immobilization on a support, and further offered a practical perspective on the ultimate viability of such approaches. See G. Szczepaniak et al., *Green Chem.* 16, 4474 (2014).

Figure 8:
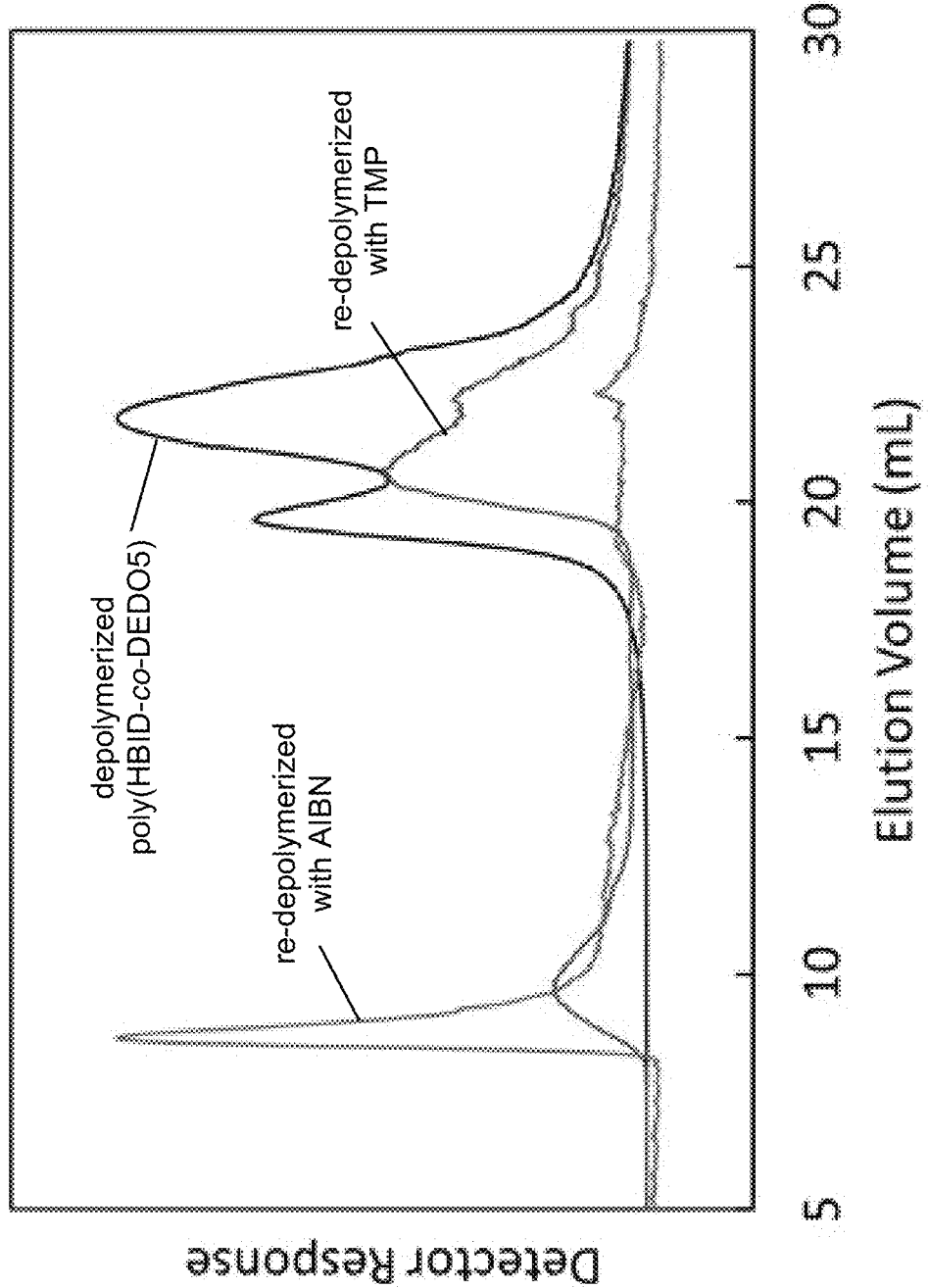
FIG. 8 shows GPC chromatographs of crosslinked PU poly(HBID-co-DEDO5) depolymerized with 2 mol. % HG2 and subsequently repolymerized using thiol-ene polymerization (by addition of TMP) or using free-radical polymerization (by addition of AIBN).

Finally, the potential for recycling or reuse of the metathesis depolymerization products into value-added materials is a consideration. As the depolymerization products are multifunctional vinyl and cycloalkene compounds, it is anticipated that several strategies can be employed for re-polymerization of these products. Indeed, Neary et al. recently reported the re-polymerization of depolymerized polypentenamers through thiol-ene chemistry performed on cyclopentene chain ends. See W. J. Neary et al., *J. Am. Chem. Soc.* 141, 14220 (2019). Similarly, as described above, metathesis can be used to depolymerize the crosslinked PU poly(HBID-co-DEDO5) in THF. Thereafter, either trimethylolpropane tris(3-mercaptopropionate) (TMP) can be added at stoichiometric equivalence ([SH]/[C=C]=1) or azobisisobutyronitrile (AIBN) can be added at 1% relative to the initial weight of poly(HBID-co-DEDO5). After re-polymerization at 60° C. for 24 hr, GPC chromatographs (FIG. 8) indicated conversion of the depolymerized mixtures to polymer, albeit only partial in the former case. The polymers thus formed were extremely high molecular weight (>$10^7$ g/mol), consistent with the multi-functional nature of the metathesis-depolymerized products.

According to the invention, a variety of polymer chemistries can be rendered depolymerizable by this method, including, but not limited to, epoxies, polyesters, and polyamides, simply by modifying the nature of the polymerizable groups in the initial monomer structure (i.e., the $R_1$ group in FIG. 2). There is a broad and critical need for new polymers with readily accessible routes to depolymerization in order to expand the use of recyclable, reusable, or otherwise degradable polymer products in large-scale commercial applications that currently generate immensely troublesome volumes of permanent waste. As such, the invention can be quite useful in rendering existing polymer materials degradable across a variety of technology sectors. From a narrow perspective, the polyurethanes (in particular, those based on PMDI) described above are analogues of existing commercial polyurethanes used primarily in foams and encapsulation. These existing materials are extremely difficult to remove, due to the permanency of their chemical structures. The depolymerizable polyurethanes described above can be adapted to replace the existing materials with an easily removable version.

The present invention has been described as novel polymers depolymerizable by metathesis of cleavable units. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A depolymerizable polymer, comprising a condensation polymer, wherein a monomeric unit of the condensation polymer is formed by reacting a functional group of a cleavable monomer, comprising two or more double bonds, at least one double bond placed in a main-chain configuration and at least one double bond placed in a side-chain configuration, with a different monomer, and wherein the cleavable monomer is cleavable by ring-closing metathesis.

2. The depolymerizable polymer of claim 1, wherein the functional group of the cleavable monomer comprises a hydroxyl, amino, epoxide, isocyanate, aldehyde, anhydride, carboxyl group, or other non-vinyl species.

3. The depolymerizable polymer of claim 1, wherein the condensation polymer comprises a polyurethane.

4. The depolymerizable polymer of claim 3, wherein the cleavable monomer comprises 8-hydroxylinalool, (E)-nona-3,8-diene-1,5-diol, or (E)-deca-3,9-diene-1,5-diol.

5. The depolymerizable polymer of claim 1, wherein the different monomer comprises an isocyanate.

6. The depolymerizable polymer of claim 5, wherein the isocyanate comprises isophorone diisocyanate, methylene diphenyl diisocyanate, or hexamethylene diisocyanate.

7. The depolymerizable polymer of claim 1, wherein the condensation polymer comprises a polymer formed from polycondensation of non-vinyl species.

8. The depolymerizable polymer of claim 7, wherein the condensation polymer comprises a polyurethane, polyamide, or polyester.

* * * * *